United States Patent [19]

Poss et al.

[11] Patent Number: 5,606,084
[45] Date of Patent: Feb. 25, 1997

[54] PROCESS OF FLUORINATING ORGANIC COMPOUNDS WITH 1-SUBSTITUTED-4-FLUORO-1,4-DIAZONIABICYCLO OCTANE SALTS

[75] Inventors: Andrew J. Poss, Kenmore; George Shia, Amherst, both of N.Y.

[73] Assignee: AlliedSignal Inc., Morris Township, N.J.

[21] Appl. No.: 477,038

[22] Filed: Jun. 7, 1995

Related U.S. Application Data

[62] Division of Ser. No. 173,297, Dec. 23, 1993, Pat. No. 5,459,267.
[51] Int. Cl.$^6$ .......................................... C07J 5/00
[52] U.S. Cl. .................. 552/600; 564/215; 544/352; 568/775; 568/656; 560/30; 570/206
[58] Field of Search ............................ 544/352; 568/775, 568/656; 552/600; 564/215; 560/30; 570/206

[56] References Cited

U.S. PATENT DOCUMENTS

| | | | |
|---|---|---|---|
| 3,038,903 | 6/1962 | Farkas et al. | 260/268 |
| 4,973,697 | 11/1990 | Umemoto et al. | 546/295 |
| 5,086,178 | 2/1992 | Banks | 544/351 |
| 5,367,071 | 11/1994 | Syvret | 540/472 |

FOREIGN PATENT DOCUMENTS 0478210  4/1992  European Pat. Off. .

OTHER PUBLICATIONS

Banks et al., 1-Alkyl-4-fluoro-1,4-diazoniabicyclo[2.2.2] octane Salts: a Novel Family of Electrophilic Fluorinating Agents, *J. Chem. Soc., Chem. Commun.*, Jan. 29, 1992, p. 595.

Farkas et al., "Some Derivatives of 1,4-Diazabicyclo(2.2.2)octane (Triethylenediamine)", *J. Chem. Eng. Data*, vol. 13, No. 2, Apr. 1968.

Lal, "Site-Selective Fluorination of Organic Compounds Using 1-Alkyl-4-fluoro-1,4-diazabicyclo[2.2.2]octane Salts (Selectfluor Reagents)," *J. Org. Chem.* 1993, 58, 2791-2796.

Murtagh, V., "Electrophilic Fluorination: An Introduction," *Performance Chemicals*, Aug./Sep. 1991, p. 36.

Umemoto et al., "N-Fluoropyridinium Triflate and Its Analogs, The First Stable 1:1 Salts of Pyridine Nucleus and Halogen Atom" *Tetrahedron Letters*, vol. 27, No. 28 (1986), pp. 3271-3274.

Gilicinski et al., "On the relative power of electrophilic fluorinating reagents of the N-F class," *J. Fluorine Chemistry*, 59, (1992) 157-162.

Organic Chemistry, Third Edition, R. T. Morrison and R. N. Boyd, p. 751.

*Primary Examiner*—Charles T. Jordan
*Assistant Examiner*—Anthony R. Chi
*Attorney, Agent, or Firm*—Jay P. Friedenson

[57] ABSTRACT

The present invention relates to the preparation and uses of 1-substituted-4-fluoro-1,4-diazoniabicyclo[2.2.2]octane salts, specifically 1-hydroxyl-4-fluoro-1,4-diazoniabicyclo [2.2.2]octane salts as reagents for the introduction of fluorine in organic compounds.

3 Claims, No Drawings

PROCESS OF FLUORINATING ORGANIC COMPOUNDS WITH 1-SUBSTITUTED-4-FLUORO-1,4-DIAZONIABICYCLO OCTANE SALTS

This application is a division of application Ser. No. 08/173,297, filed Dec. 23, 1993, now U.S. Pat. No. 5,459,267.

BACKGROUND OF THE INVENTION

The present invention relates to the preparation and uses of 1-substituted-4-fluoro-1,4-diazoniabicyclo[2.2.2]octane salts, specifically 1-hydroxyl-4-fluoro-1,4-diazoniabicyclo[2.2.21]octane salts as reagents for the introduction of fluorine in organic compounds.

Electrophilic fluorinating agents, characterized by a structure containing an N—F bond, have been shown to be stable, easily handled reagents capable of fluorinating organic molecules. These compounds have been reviewed by Murtage in Perform. Chem. (1991) 6, 36 and (1992) 7, 27. The only fluorinating agents not covered by the review are N-fluoro-2-halopyridinium-6-sulfonates described by Umemoto in U.S. Pat. No. 4,973,697.

SUMMARY OF THE INVENTION

The 1-substituted-4-fluoro-1,4-diazoniabicyclo[2.2.2]octane salts have the general structure shown below:

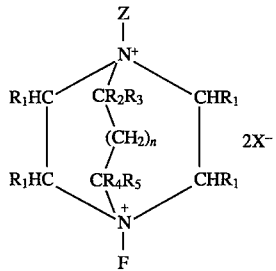

wherein, Z is OH, OR, OC(O)R, SO3, SO2R, NO2, NO, or P(O)(OR)2 with R being an aryl or $C_1$–$C_8$ alkyl, where n represents 0, 1 or 2; each $R_1$, $R_2$, $R_3$, $R_4$ and $R_5$ independently represents hydrogen, $C_1$–$C_8$ alkyl, aryl, C1–C8 alkyl; and each X- independently represents a counterion or 2X- represents a single divalent counterion. Further embodiments and advantages of the present invention will become apparent from the following description.

DETAILED DESCRIPTION OF THE INVENTION

Fluorinating agents of the N—F type have been formed from 1,4-diazabieyclo[2.2.2]octane salts. These fluorinating agents are desclosed in U.S. Pat. No. 5,086,178 to Banks. The Banks' agents are 1-substituted-4-fluoro-1,4-diazoniabicyclo[2.2.2]octane salts; however, Banks forms a nitrogen-carbon (N—C) bond with the nitrogen at position 1 of the tricyclic ring system. As described by Banks, the 1-substituent is a quaternized organic group which forms the N—C bond to make the nitrogen at the 1 position a quaternary nitrogen.

The novel electrophilic fluorinating agents of the present invention do not form a quaternized N—C bond. We have discovered that numerous substituents can be used at the 1 position nitrogen other than Banks' quaternizing organic groups which form the N—C bond. The substituent groups represented by Z in this invention depict nitrogen-heteroatom (N—Z) bonds and are the result of oxidation of the nitrogen atom. These substituent groups are as follows: OH, OR, OC(O)R, SO3, SO2R, NO2, NO, PO(O)(OR)2, with R being an aryl or C1–C8 alkyl.

In one of the preferred embodiments, the 1-position substituent (or 1-substituent) group is selected from one of the above inorganic groups. In alternatively preferred embodiments, the 1-substituent is selected from OH, OR and OC(O)R. These particular substituent groups are preferred since they offer a simplified and economical method of preparation for forming the desired fluorinating agent, especially when compared to the N—C quaternizing organic substituent employed by Banks The preferred groups, OH, OR OC(O)R are the result of the oxidation of nitrogen with the inexpensive oxidation agent, hydrogen peroxide, which in the case of OR or OC(C)R is followed by alkylation or acylation. The oxidation of nitrogen and the substitution at oxygen have the cost advantages of inexpensive reagents and solvent, short reaction times, and minimal waste due to the ability to recycle solvents and straight forward work-ups.

The quaternization of a tertiary nitrogen with simple primary alkyl halides is taught as a straightforward process. However, those groups used to quaternize the nitrogen in position 1 of 1,4-diazoniabicyclo[2.2.2]octane as described in U.S. Pat. No. 5,086,178 are exceptions to the generalization. The quaternization of amines with dichloromethane requires either high pressure or several days at standard pressure to complete, as described by Almarzoqi in Tetrahedron, 42 601 (1986). The reaction is further complicated by the formation of bis-ammonium salts. The reagents for the manufacture of the 1,1,1-trifluoroethyl substituent, namely trifluoroethyltriflate, is very expensive.

The fluorinating agents employing OH, —OR and OC(O)R are more preferred since these groups are more electronegative than the N—C forming quaternizing groups disclosed by Banks. See Cary and Sundberg, "Advanced Organic Chemistry", which is incorporated herein by reference, for a listing of the electronegativity values. Basically, the increased electronegativity corresponds to improved fluorination ability.

Umemoto demonstrated in J. Am. Chem. Soc. 112, 8563 (1990) that the electrophilic fluorinating ability of N-fluoropyridinium salts varies greatly with the electron density at the N—F site. He reported that the presence of highly electronegative groups on the pyridine nucleus increased the ease of electrophilic fluorine transfer. N-fluoro-1,3,5-trimethylpyridinium triflate is less reactive than N-fluoro-3,5-dichloropyridinium triflate which is not as reactive as N-fluoro-pentachloropyridinium triflate (electronegativity of CH3 is 2.3 compared to 3.03 for Cl). This study showed that the greater the electronegativity of the group affecting the N—F bond, the greater the ease of electrophilic fluorine transfer. The preferred substituents, OH, OR, and OC(O)R, have an electronegativity of 3.7. Since the presence of an O—N bond at the N-1 position of 1,4-diazonabicyclo[2.2.2]octane affects the N—F bond in a manner similar to that of the pyridinium salts, the presence of the preferred highly electronegative groups leads to extremely powerful fluorinating agents.

The most preferred substituent is the OH group. It is surprising that an OH group can be employed since it is an uncommon, if not unknown, substituent group for an N—F type fluorinating agent. The fluorinating agent which employs the OH group possesses the advantages of enhanced electronegativity, ease of preparation and decreased manufacturing costs.

We were surprised to find that 1-hydroxyl-4-fluoro-1,4-diazoniabicyclo[2.2.2]octane salts (Z=OH) could be prepared despite the relatively high electronegativity of the hydroxyl functionality (3.7). The electronegativity of the OH group is less than only two other functionalities: F (3.95) and NH3+ (3.8), (see Cary and Sundberg, "Advanced Organic Chemistry"). Banks has reported in J. Chem. Soc. Chem. Commun. (1992) 595 that all attempts to prepare 1,4-difluoro-1,4-diazoniabicyclo[2.2.2]octane salts (where the 1 substituent or Z is F) were unsuccessful. Within the Banks Reagent series, the electronegativity of the quaternary organic group varies from 2.3 for R=CH3 to less than 3.35 for R=CH2CF3. (The electronegativity of R=CF3 is 3.35; The insulating methylene group lowers the effect of the trifluoromethyl group), while the electronegativity of fluorine is 3.95. From Banks' statement that the reagent where Z=F cannot be formed but that the other Banks reagents are stable, one would conclude that any 1-substituent with an electronegativity relatively similar to that of fluorine would not be accessible. Because of the relatively high electronegativity value for the OH group, which has an electronegativity value less than only two other functionalities: F (3.95) and NH3+ (3.8), it was not expected that the 1-hydroxyl-1,4-diazoniabicyclo[2.2.2]octane could be fluorinated to form the 1-hydroxyl-4-fluoro-1,4-diazoniabicyclo[2.2.2]octane salts.

Additional embodiments with respect to the other ring substituents, $R_1$–$R_5$, and X—, the counteranion, are discussed herein.

When any of $R_1$ to $R_5$ is other than hydrogen, it is preferably benzyl, phenyl or, especially, $C_1$–$C_4$ alkyl, particularly methyl. It will be understood that due to steric considerations it is not possible to obtain compounds of this Formula with all possible combinations of $R_1$ to $R_5$ values. In more preferred embodiments, no more than one $R_1$ at the 2 and 3 ring positions and no more than one $R_1$ at the 5 and 6 positions will be other than hydrogen. It is presently further preferred that all $R_1$ are hydrogen and usually no more than one of $R_2$, $R_3$, $R_4$ and $R_5$ is other than hydrogen.

The counterion(s) represented by 2X— can be selected for with a variety of anion(s), which can be, not necessarily, weakly-nucleophilic. Umemoto in Tetrahedron Letters (1986) 27, 3271 reported that a weakly or non-nucleophilic stabilizing ion is preferred to avoid the complicating side reaction of the counter ion attacking or adding to the electrophilic N—F containing compound. Suitable anions include fluorosulfate (SO3F—); alkyl sulfates, especially methyl sulfate (CH3SO3—); perfluoroalkylsulfonates, preferably triflate (CF3SO3—) and nonaflate (C4F9SO3—); arenesulfonates, especially tosylate (i.e., p-toluenesulfonate; CH3C6H4SO3—); alkylcarboxylates: perfluoroalkylcarboxylates; tetrafluoroborate (BF4—); tetraphenylborate (Ph4B—); hexafluorophosphate (PF6—); hexafluoroantimonate (SbF6—); chlorate (ClO3—); and sulfate (SO4—=2X—). The presently preferred anions are either tetrafluoroborate or triflate.

In the Formula of this invention, it is preferred that n is 0 and each $R_1$ is hydrogen (i.e. that the compound of Formula shown are derivatives of tetraethylenediamine). Thus, accordingly, in one of the most preferred embodiments the novel fluorinating agents of this invention are 1-hydroxyl-4-fluoro-1,4-diazoniabicyclo[2.2.2]octane derivatives.

The preparation of 1-hydroxyl-4-fluoro-1,4-diazoniabicyclo[2.2.2]octane bis(tetrafluoroborate) can be accomplished under a variety of conditions. The method for introducing the tetrafluoroborate counterion can be varied. The BF4— can originate from: one equivalent of sodium tetrafluoroborate and one equivalent of fluoroboric acid; two equivalents of sodium tetrafluoroborate; one equivalent of tetrafluoroboric acid and an equivalent of boron trifluoride etherate; one equivalent of tetrafluoroboric acid and an equivalent of boron trifluoride gas; or two equivalents of boron trifluoride gas and an equivalent of water. The temperature can be varied from –40° to 20° C.

The preparation of the above novel reagent has the manufacturing advantage over the chloromethyl substituted derivation of the Banks reagent in that it requires one less step and does not require a counter-ion exchange reaction. Thus, our preparation avoids unnecessary extended reaction times and/or unconventional reaction conditions. At present, the only commercially available member of the Banks Reagents is 1-(chloromethyl)-4-fluoro-1,4-diazabicyclo[2.2.2]octane bis(tetrafluoroborate), F-TEDA-BF$_4$, and to our knowledge it is prepared in four steps. One step involves the alkylation of tetramethylenediamine with dichloromethane which requires either high pressure or long reaction times (days) to afford a reasonable yield. 1-Hydroxyl-4-fluoro-1,4-diazoniabicyclo[2.2.2]octane salts are prepared by oxidation of triethylenediamine to its corresponding N-oxide with hydrogen peroxide (2—4 hours), as described by Farkas in J. Chem. Eng. Data (1968) 13, 278, followed by fluorination in a suitable solvent, in the presence of non- or weakly nucleophilic counterions such as tetrafluoroborate or triflate.

It was also discovered that water can be used as the solvent in the manufacture of 1-hydroxyl-4-fluoro-1,4-diazoniabicyclo[2.2.2]octane bis(tetrafluoroborate), NFTh. Treatment of an aqueous solution of 1,4-diazabicyclo[2.2.2]octane mono-N-oxide, one equivalent of tetrafluoroboric acid, and one equivalent of boron trifluoride gas with fluorine at 5° C. affords NFTh in good yield. The synthesis of tetrafluoroborate salts of fluorinating agents in water is unprecedented due to their hydroscopic nature. This methodology can be expanded to the preparation of the N—F reagents like the Banks reagent, F-TEDA-BF$_4$, which are disclosed in U.S. Pat. No. 5,086,178 and is incorporated herein by reference. The Banks reagents have the following general formula:

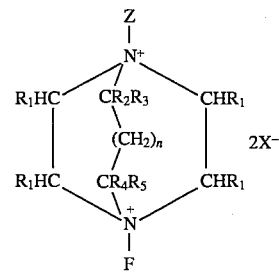

wherein, n represents 0, 1 or 2; each R represents a quaternizing organic group; each $R_1$, $R_2$, $R_3$, $R_4$ and $R_5$ independently represents hydrogen, $C_1$–$C_6$ alkyl, aryl, $C_1$–$C_6$ alkyl-substituted aryl or aryl-substituted $C_1$–$C_6$ alkyl and each X—independently represents a counterion or 2X— represents a single divalent counterion.

The use of nonflammable and less expensive water in place of acetonitrile represents a process improvement from the standpoint of both safety and cost.

The synthesis of 1-hydroxyl-4-fluoro-1,4-diazoniabicyclo[2.2.21]octane bis(tetrafluoroborate), NFTh, has the additional manufacturing advantage in that the entire preparation can be conducted in "one pot" with water as the solvent. Treatment of 1,4-diazoniabicyclo[2.2.2]octane in water with a peroxide, preferably, hydrogen peroxide, in a manner similar to U.S. Pat. No. 3,038,903 affords an aqueous solution of 1,4-diazabicyclo[2.2.2]octane mono-N-oxide. U.S. Pat. No. 3,038,903 is incorporated herein by reference. After addition of one equivalent of tetrafluoroboric acid and one equivalent of boron trifluoride gas, the solution is reacted with fluorine at a temperature sufficient to give a good yield of 1-hydroxyl-4-fluoro-1,4-diazoniabicyclo[2.2.2]octane bis(tetrafluoroborate). Preferably, the temperature ranges from about 0° C. to about 30° C., and more preferably, from about 5° C. to about 15° C., with 5° C. being one of the preferred temperature for the reaction. The use of the "one pot" procedure has the advantage of avoiding the manufacturing costs associated with multi-reactor processes and the toxicity and safety problems associated with handling potentially toxic intermediates.

Another embodiment of this invention relates to a process for the electrophilic fluorination of an organic compound which comprises the step of: reacting one equivalent of an organic compound with at least one equivalent of a novel fluorinating agent of this invention. The novel fluorinating reagents of this invention can be used for the fluorination of steroidal dienol acetates, eneamides, aromatics and olefins; for example: 3,5-pregnadien-3,21-diol-20-one diacetate, acetanilide, polyurethane, a-methylstyrene, anisole and phenol. The reaction times and the needs of industry are satisfactorily met or are exceeded by our novel reagents.

The fluorination ability of this new agent can exceed that of 1-(chloromethyl)-4-fluoro-1,4-diazoniabicyclo[2.2.2]octane bis(tetrafluoroborate), or F-TEDA-BF$_4$, for some reactions as shown in the Comparative Examples.

The present invention is more fully illustrated by the following non-limiting examples.

It is noted that the novel fluorinating agents of this invention can be prepared by reacting the N-substituted-1,4 diazabicyclo[2.2.2]octane compound in an organic solvent, water or mixtures thereof in the presence of a counteranion and elemental fluorine in an amount and at a temperature sufficient to form the desired N-substituted-N'-fluoro-1,4 diazoniabicyclo[2.2.2]octane compound.

A wide variety of solvents may be used although water, or solvent mixtures comprising 50 percent or more by volume of water, are preferred. Illustrative of useful solvents are acetonitrile, propionitrile, methylene chloride, chloroform, trichlorofluoromethane, trichlorofluoromethane and mixtures thereof.

EXAMPLE 1

1-Hydroxy4-fluoro-1,4-diazoniabicyclo[2.2.2]octane bis(tetrafluoroborate), NFTh, (from 1,4-diazabicyclo[2.2.21]octane N-oxide, 1 equivalent of sodium tetrafluoroborate and 1 equivalent of tetrafluoroboric add).

1,4-Diazabicyclo[2.2.21]octane N-oxide was prepared by the reaction of 1,4-diazabicyclo[2.2.21]octane with hydrogen peroxide as described by Farkas in J. Chem. Eng. Data (1968) 13, 278. A solution of 1,4-diazabicyclo[2.2.21]octane N-oxide (1.28 g, 10 mmole), sodium tetrafluoroborate (1.1 g, 10 mmole), and tetrafluoroboric acid (50% solution, 1.83 g, 10 mmole) in acetonitrile (250 mL) was cooled to −35° C. and treated with a mixture of fluorine in nitrogen (10% V/V, 14 mmole). The reaction was evaporated, the remaining solid washed with acetone and dried to afford 1.23 grams of 1-hydroxyl-4-fluoro-1,4-diazoniabicyclo[2.2.2]octane bis(tetrafluoroborate) (38% yield); m.p. 336–8° C.; $^1$H NMR (D2O): d 5.0 (m, 6H), 4.6 (m, 6H); $^{13}$C NMR (D2O): d 61.6 (d, J=15.5 Hz), 62.3 (d, J=6.2 Hz); $^{19}$F (D2O): d 41 (1F), —150 (8F); 15N (D2O): d —207.5 (d, J=84 Hz), —275.9. Anal. Calcd for C$_6$H$_{13}$B$_2$F$_9$N$_2$O: C, 22.40; H, 4.07; N, 8.70; B, 6.72. Found: C, 22.69; H, 4.25; N, 8.80; B, 6.39.

EXAMPLE 2

1-Hydroxyl-14-fluoro-1,4-diazoniabicyclo[2.2.2]octane bis(tetrafluoroborate), NFTh, (from 1,4-diazabicyclo[2.2.2]octane N-oxide, 1 equivalent of boron trifluoride etherate and 1 equivalent of tetrafluoroboric acid).

A solution of 1,4-diazabicyclo[2.2.2]octane N-oxide (2.56 g, 20 mmole), boron trifluoride etherate (2.4 mL, 20 mmole), and tetrafluoroboric acid (50% solution, 3.66 g, 20 mmole) in acetonitrile (250 mL) was cooled to 8° C. and treated with a mixture of fluorine in nitrogen (10% V/V, 52 mmole). The reaction was evaporated, the remaining solid washed with acetone and dried to afford 4.8 grams of 1-hydroxyl-4-fluoro-1,4-diazoniabicyclo[2.2.2]octane bis(tetrafluoroborate) (75% yield).

EXAMPLE 3

1-Hydroxyl-4-fluoro-1,4-diazoniabicyclo[2.2.2]octane bis(tetrafluoroborate), NFTh, (from 1,4-diazabicyclo[2.2.21]octane N-oxide and 2 equivalents of sodium tetrafluorborate).

A solution of 1,4-diazabicyclo[2.2.21]octane N-oxide (1.26 g, 9.8 mmole) and sodium tetrafluorobroate (1 g, 9.1 mmole) in acetonitrile (250 mL) was cooled to 8° C. and treated with a mixture of fluorine in nitrogen (10% V/V, 30 mmole). The reaction was evaporated, the remaining solid washed with acetone and dried to afford 1.03 grams of 1-hydroxyl-4-fluoro-1,4-diazoniabicyclo[2.2.2]octane bis(tetrafluoroborate) (70% yield).

EXAMPLE 4

1-Hydroxyl-4-fluoro-1,4-diazoniabicyclo[2.2.2]octane bis(tetrafluoroborate), NFTh, (from 1,4-diazabicyclo[2.2.2]octane N-oxide, 2 equivalents of boron trifluoride gas and 1 equivalent of water).

A solution of 1,4-diazabicyclo[2.2.2]octane N-oxide (12.8 g, 0.1 mole), water (1.8 mL, 0.1 mole) and boron trifluoride (13.6 g, 0.2 mole) in acetonitrile (250 mL) was cooled to 8° C. and treated with a mixture of fluorine in nitrogen (10% V/V, 0.2 mole). The reaction was evaporated, the remaining solid washed with acetone and dried to afford 22 grams of 1-hydroxyl-4-fluoro-1,4-diazoniabicyclo[2.2.2]octane bis(tetrafluoroborate) (68% yield).

EXAMPLE 5

1-Hydroxyl-4-fluoro-1,4-diazoniabicyclo[2.2.2]octane bis(tetrafluoroborate), NFTh, (from 1,4-diazabicyclo[2.2.2]octane N-oxide, 1 equivalent of boron trifluoride and 1 equivalent of tetrafluoroboric acid).

A solution of 1,4-diazabicyclo[2.2.2]octane N-oxide (12.8 g, 0.1 mole), boron trifluoride gas (6.8 g 0.1 mole), and tetrafluoroboric acid (50% solution, 12 g, 0.1 mole) in acetonitrile (200 mL) was cooled to 8° C. and treated with a mixture of fluorine in nitrogen (10% V/V, 0.15 mole). The reaction was evaporated, the remaining solid washed with acetone and dried to afford 21 grams of 1-hydroxyl-4-fluoro-1,4-diazoniabicyclo[2.2.2]octane bis(tetrafluoroborate) (65% yield).

EXAMPLE 6

1-Hydroxyl-4-fluoro-1,4-diazoniabicyclo[2.2.2]octane bis(tetrafluoroborate), NFTh, (from 1,4-diazabicyclo[2.2.2]octane N-oxide, 1 equivalent of boron trifluoride and 1 equivalent of tetrafluoroboric acid; water as solvent).

A solution of 1,4-diazabicyclo[2.2.2]octane N-Oxide (25.6 g, 0.2 mole), boron trifluoride gas (13.6 g, 0.2 mole), and tetrafluoroboric acid (10 M solution, 20 mL, 0.2 mole) in water (400 mL) was cooled to 8° C. and treated with a mixture of fluorine in nitrogen (10% V/V, 0.2 mole). The reaction was evaporated, the remaining solid washed with acetone and dried to afford 51.4 grams of 1-hydroxyl-4-fluoro-1,4-diazoniabicyclo[2.2.2]octane bis(tetrafluoroborate) (80% yield).

EXAMPLE 7

1-(chloromethyl)-4-fluoro-1,4-diazabicyclo[2.2.2]octane bis(tetrafluoroborate), F-TEDA-BF$_4$, (from 1-Chloromethyl-4-aza-1-azoniabicyclo[2.2.2]octane tetrafluoroborate, 1 equivalent of boron trifluoride; water as solvent).

1-Choloromethyl-4-aza-1-azoniabicyclo[2.2.2]octane tetrafluoroborate was prepared as described by Banks in U.S. Pat. No. 5,086,178. A solution of 1-chloromethyl-4-aza-1-azoniabicyclo [2.2.2]octane tetrafluoroborate (24.8 g, 0.1 mole) and boron trifluoride gas (6.2 g, 0.1 mole) in water (200 mL) was cooled to 10° C. and treated with a mixture of fluorine in nitrogen (10% V/V, 0.26 mole). The reaction was evaporated, the remaining solid washed with acetone and dried to afford 51.4 grams of 1-(chloromethyl)-4-fluoro-1,4-diazabicyclo[2.2.2]octane bis tetrafluoroborate) (79% yield).

EXAMPLE 8

1-hydroxy-14-fluoro-1,4-diazoniabicyclo[2.2.2]octane bis(tetrafluoroborate), NFTh, (from 1,4-diazabicyclo[2.2.2]octane, hydrogen peroxide, 1 equivalent of boron trifluoride and 1 equivalent of tetrafluoroboric acid; water as solvent, "one pot synthesis").

To a solution of 1,4-diazabicyclo[2.2.2]octane (11.2 g, 0.1 mole) in water (100 mL) was added 30% hydrogen peroxide (22.8 mL) while maintaining the temperature between 15°and 20° C. The reaction was stirred at room temperature (20–22° C.) overnight. Next, boron trifluoride gas (6.8 g, 0.1 mole) and tetrafluoroboric acid (50% solution, 10 mL, 0.1 mole) were added, the solution cooled to 9° C. and treated with a mixture of fluorine in nitrogen (10% V/V, 0.125 mole). The reaction was evaporated, the remaining solid washed with acetone and dried to afford 30 grams of 1-hydroxyl-4-fluoro-1,4-diazoniabicyclo[2.2.2]octane bis(tetrafluoroborate) (93% yield).

FLUORINATION REACTIONS

Example A

To a solution of 3,5-pregnadien-3,21-diol-20-one diacetate (10 mg, 0.026 mmole) in acetonitrile (0.3 mL) was added 1-hydroxyl-4-fluoro-1,4-diazoniabicyclo[2.2.2]octane bis(tetrafluoroborate) (15 mg, 0.047 mmole 1.8 equ.) and the reaction stirred at room temperature for 15 min. The mixture was diluted with ether (2 mL), washed with water (1 mL), 10% HCl (1 mL), and sat NaHCO$_3$ (1 mL), filtered through anhydrous MgSO$_4$, and evaporated to afford 9 mg (89% yield) of a 1:2.2 mixture of 6- to 6-fluoro 4-pregnen-21-ol-3,20-dione acetate.

Example B

To a solution of acetanilide (135 mg, 1 mmole) in acetonitrile (2 mL) was added 1-hydroxyl-4-fluoro-1,4-diazoniabicyclo[2.2.2]octane bis(tetrafluoroborate)354 mg, 1.1 mmole 1.1 equ.) and the reaction stirred at 40° C. for 6 h. The mixture was diluted with ether (2 mL), washed with water (1 mL), 10% HCl (1 mL), and sat NaHCO$_3$ (1 mL), filtered through anhydrous MgSO$_4$, and evaporated to afford 142 mg (84% yield) of a 1:2 mixture of 4- to 2-fluoroacetanilide.

Example C

To a solution of phenylurethane (165 mg, 1 mmole) in acetonitrile (2 mL) was added 1-hydroxyl-4-fluoro-1,4-diazoniabicyclo[2.2.2]octane bis(tetrafluoroborate) (354 mg, 1.1 mmole 1.1 equ.) and the reaction stirred at 80° C. for 6 h. The mixture was diluted with ether (2 mL), filtered through anhydrous MgSO$_4$, and evaporated to afford 162 mg (88% yield) of a 2.3:1 mixture of 4- to 2-fluorophenylurethane.

Example D

To a solution of alpha-methylstyrene (0.13 mL, 1 mmole)and methanol (0.05 mL, 1.1 mmole) in acetonitrile (10 mL) was added 1-hydroxyl-4-fluoro-1,4-diazoniabicyclo[2.2.2]octane bis(tetrafluoroborate) (330 mg, 1.02 mmole 1.02 equ.) and the reaction stirred at room temperature for 24 h. The mixture was diluted with ether (2 mL), filtered through anhydrous MgSO$_4$, and evaporated to afford 130 mg (85% yield) of 1-fluoro-2-methoxy-2-phenylpropane.

Example E

To a solution of alpha-methylstyrene (0.13 mL, 1 mmole) and water (0.02 mL, 1.1 mmole) in acetonitrile (10 mL) was added 1-hydroxyl-4-fluoro-1,4-diazoniabicyclo [2.2.2]octane bis(tetrafluoroborate) (330 mg, 1.02 mmole 1.02 equ.) and the reaction stirred at room temperature for 24 h. The mixture was diluted with ether (2 mL), filtered through anhydrous MgSO$_4$, and evaporated to afford 110 mg (71% yield) of 1-fluoro-2-hydroxy-2-phenylpropane.

Example F

To a solution of phenol (94 mg, 1 mmole) in acetonitrile (1 mL) was added 1-hydroxyl-4-fluoro-1,4-diazoniabicyclo [2.2.2]octane bis(tetrafluoroborate) (354 mg, 1.1 mmole 1.1 equ.) and the reaction stirred at 40° C. for 5 h. The mixture was diluted with ether (2 mL), filtered through anhydrous MgSO$_4$, and evaporated to afford 90 mg (80% yield) of a 1.2:1 mixture of 4- to 2-fluorophenol.

COMPARATIVE EXAMPLES

The fluorination ability of this new agent can exceed that of 1-(chloromethyl)-4-fluoro-1,4-diazabicyclo[2.2.2]octane bis(tetrafluoroborate), or F-TEDA-BF$_4$, for some reactions as shown in the following Comparative Examples.

Example G

Lower reaction temperatures can be used in the fluorination of aromatics with NFTh because our reagent is more reactive F-TEDA-BF$_4$. For example, when the same conditions as described in Comparative example G for fluorination of anisole were used with NFTh, only decomposition products were observed. However, by reacting anisole with NFTh at room temperature for 5 hrs., the desired products are obtained.

To a solution of anisole (0.11 mL, 1 mmole) in acetonitrile (2 mL) was added 1-hydroxyl-4-fluoro-1,4-diazoniabicyclo[2.2.2]octane bis(tetrafluoroborate) (326 mg, 1 mmole, 1 equ.) and the reaction stirred at room temperature for 5 h. The mixture was diluted with ether (2 mL), washed with water (1 mL), 10% HCl (1 mL), and sat NaHCO$_3$ (1 mL), filtered through anhydrous MgSO$_4$, and evaporated to afford 104 mg (83% yield) of a 1:2.4 mixture of 2- to 4-fluoroanisole.

Comparative Example G

The reaction of anisole with F-TEDA-BF$_4$ at 4.0° C. for 6 hours afforded a 1:1 mixture of 2- and 4-fluoroanisole [Banks, R. E.; et. al. J. Chem. Soc. Chem. Commun. (1992) 595].

Example H

NFTh is more stereospecific than F-TEDA-BF$_4$ in the fluorination of enol ethers as evidenced by example H versus comparative example H (4-tert-butyl-1-ethoxycyclohexene to primarily cis-4-tert-butyl-2-fluorocyclohexanone).

To a solution of 4-tert-butyl-1-ethoxycyclohexene (50 mg 0.27 mmole) in acetonitrile (0.6 mL) was added 1-hydroxyl-4-fluoro-1,4-diazoniabicyclo[2.2.2]octane bis(tetrafluoroborate) (97 mg, 0.3 mmole) and the reaction stirred at 22° C. for 6 h, then 60° C. for 12 h. The mixture was diluted with ether (2 mL), washed in 10% HCl (2 mL), sat NaHCO$_3$ (2 mL), filtered through anhydrous MgSO$_4$, and evaporated to afford 29 mg of a 12.8:1 mixture of cis- to trans-4-tert-butyl-2-fluorocyclohexanone contaminated with 43% 4-ten-butylcyclohexanone.

Comparative Example H

To a solution of 4-tert-butyl-1-ethyoxycyclohexene (50 mg, 0.27 mmole) in acetonitrile (0.6 mL) was added 1-(chloromethyl)-4-fluoro-1,4-diazoniabicyclo[2.2.2]octane bis(tetrafluoroborate) (106 mg, 0.3 mmole) and the reaction stirred at 22° C. for 6-h, then 60° for 12 h. The mixture was diluted with ether (2mL), washed with 10% HCl (2 mL), sat NaHCO$_3$ (2 mL), filtered through anhydrous MgSO$_4$, and evaporated to afford 21 mg of a 3.3:1 mixture of cis- to trans-4-tert-butyl-2-fluorocyclohexanone contaminated with 45% 4-tert-butylcyclohexanone.

Example I

NFTh is more regioselective than F-TEDA-BF$_4$ in the fluorination of napthols as evidenced by example I versus comparative example I (2-hydroxynapthalene to primarily 1-fluoro-2-hydroxynapthlene).

To a solution of 2-hydroxynapthalene (72 mg, 0.5 mmole) in acetonitrile (1 mL) was added 1-hydroxyl-4-fluoro-1,4-diazoniabicyclo[2.2.2]octane bis(tetrafluoroborate) (177 mg, 0.55 mmole) and the reaction stirred at 22° C. for 6 h. The mixture was diluted with ether (2 mL), filtered through anhydrous MgSO$_4$, and evaporated to afford 71 mg of a 16.7:6.4:1 mixture of 1-fluoro-2-hydroxynapthlene ($^{19}$F NMR-156) to 3-fluoro-2-hydroxynapthlene ($^{19}$F NMR -153) to 1,1-difluoro-2-oxo-1,2-dihydronapthalene ($^{19}$F NMR-102).

Comparative Example I

To a solution of 2-hydroxynapthalene (72 mg, 0.:5 mmole) in acetonitrile (1 mL) was added 1-(chloromethyl)-4-fluoro-1,4-diazoniabicyclo[2.2.2]octane bis(tetrafluoroborate) (195 mg, 0.55 mmole) and the reaction stirred at 22° C. for 6 h. The mixture was diluted with ether (2 mL), filtered through anhydrous MgSO$_4$, and evaporated to afford 74 mg of a 4.7:1:2.2 mixture of 1-fluoro-2-hydroxynapthlene ($^{19}$F NMR-156) to 3-fluoro-2-hydroxynapthlene ($^{19}$F NMR -153) to 1,1-difluoro-2-oxo-1,2-dihydronapthalene ($^{19}$F NMR-102).

Having described the invention in detail and by reference to preferred embodiments thereof, it will be apparent that modification and variations are possible without departing from the scope of the invention defined in the appended claims.

What we claim:

1. A process for the electrophilic fluorination of an organic compound which comprises the step of: reacting an organic compound with a 1-substituted-4-fluoro-1,4-diazoniabicyclo salt of the following formula:

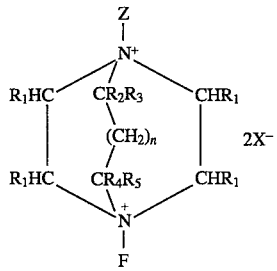

wherein, Z is selected from the group consisting of OH, OR, OC(O)R, SO$_3$, NO$_2$ and P(O)(OR)$_2$ with R being carbocyclic aryl or $C_1$–$C_8$ alkyl, where n represents 0, 1 or 2; each R$_1$, R$_2$, R$_3$, R$_4$ and R$_5$ independently represents hydrogen, $C_1$–$C_8$ alkyl, carbocyclic aryl or $C_{1-C8}$ alkyl; and each X$^-$ independently represents a counterion or 2X$^-$ represents a single divalent counterion.

2. The process of claim 1 wherein the organic compound is selected from steroidal dienol acetates, eneamides, aromatics or olefins.

3. The process of claim 1 wherein the organic compound is selected from: 3,5-pregnadien-3, 21-diol-20-one diacetate, acetanilide, phenylurethane, alpha-methylstyrene, anisole, or phenol.

* * * * *